(12) United States Patent
Qi et al.

(10) Patent No.: US 12,057,199 B2
(45) Date of Patent: *Aug. 6, 2024

(54) PREPARATION METHOD OF CONDUCTIVE GALLIUM OXIDE BASED ON DEEP LEARNING AND VERTICAL BRIDGMAN GROWTH METHOD

(71) Applicant: HANGZHOU FUJIA GALLIUM TECHNOLOGY CO. LTD., Zhejiang (CN)

(72) Inventors: Hongji Qi, Hangzhou (CN); Long Zhang, Hangzhou (CN); Duanyang Chen, Hangzhou (CN)

(73) Assignee: HANGZHOU FUJIA GALLIUM TECHNOLOGY CO. LTD., Hangzhou (CN)

( * ) Notice: Subject to any disclaimer, the term of this patent is extended or adjusted under 35 U.S.C. 154(b) by 309 days.

This patent is subject to a terminal disclaimer.

(21) Appl. No.: 17/761,322

(22) PCT Filed: Feb. 7, 2021

(86) PCT No.: PCT/CN2021/075864
§ 371 (c)(1),
(2) Date: Mar. 17, 2022

(87) PCT Pub. No.: WO2022/141760
PCT Pub. Date: Jul. 7, 2022

(65) Prior Publication Data
US 2023/0170055 A1    Jun. 1, 2023

(30) Foreign Application Priority Data
Dec. 31, 2020  (CN) .......................... 202011642153.8

(51) Int. Cl.
C30B 11/02        (2006.01)
G06N 3/0464       (2023.01)
(Continued)

(52) U.S. Cl.
CPC .............. *G16C 20/10* (2019.02); *C30B 11/02* (2013.01); *G06N 3/0464* (2023.01); *G06N 3/08* (2013.01); *G16C 20/70* (2019.02)

(58) Field of Classification Search
CPC ....... C30B 11/006; C30B 11/02; C30B 29/16; G16C 20/10; G16C 20/70; G06N 3/08; G06N 3/0464
See application file for complete search history.

(56) References Cited

U.S. PATENT DOCUMENTS

| 11,489,090 B1* | 11/2022 | Atanackovic | ..... H01L 29/66462 |
| 11,502,223 B1* | 11/2022 | Atanackovic | ......... H01L 33/002 |
| 2021/0351321 A1* | 11/2021 | Atanackovic | ...... H01L 21/02414 |

FOREIGN PATENT DOCUMENTS

| CN | 109338456 A | 2/2019 |
| CN | 110033486 A | 7/2019 |

(Continued)

OTHER PUBLICATIONS

Office Action issued on Apr. 17, 2023, in corresponding Japanese Application No. 2022-520485, 11 pages.
(Continued)

*Primary Examiner* — Robert M Kunemund
(74) *Attorney, Agent, or Firm* — Maier & Maier, PLLC

(57) ABSTRACT

A preparation method of conductive gallium oxide based on deep learning and vertical Bridgman growth method. The prediction method includes: obtaining a preparation data of the conductive gallium oxide single crystal, the preparation data includes a seed crystal data, an environmental data, a control data and a raw material data, and the raw material
(Continued)

data includes a doping type data and a conductive doping concentration; preprocessing the preparation data to obtain a preprocessed preparation data; inputting the preprocessed preparation data into a trained neural network model, and obtaining a predicted property data corresponding to the conductive gallium oxide single crystal through the trained neural network model, the predicted property data includes a predicted carrier concentration.

10 Claims, 3 Drawing Sheets

(51) Int. Cl.
 *G06N 3/08* (2023.01)
 *G16C 20/10* (2019.01)
 *G16C 20/70* (2019.01)

(56) References Cited

FOREIGN PATENT DOCUMENTS

| CN | 111028893 A | 4/2020 |
|---|---|---|
| CN | 111695287 A | 9/2020 |
| CN | 111893563 A | 11/2020 |
| JP | 2002517367 A | 6/2002 |
| JP | 200624195 A | 1/2006 |
| JP | 202059633 A | 4/2020 |
| WO | 9963134 A1 | 12/1999 |

OTHER PUBLICATIONS

Dropka et al., "Application of Artificial Neural Networks in Crystal Growth of Electronic and Opto-Electronic Materials", Crystals, 2020, vol. 10, No. 8, 19 pages.

International Search Report issued on Oct. 9, 2021 in corresponding International application No. PCT/CN2021/075864; 4 pages.

Chinese Office Action issued on Nov. 3, 2021 in corresponding application No. 202011642153.8; 16 pgs.

Su Weifeng, Crystal Growth Prediction Control Based on Neural Network "China Excellent Master's Degree Thesis Full-text Database (Information Technology Series)" Jun. 15, 2005 (Jun. 15, 2005), Issue 2, Section 1.1 and Chapter 2-4.

Mu Wenxiang, Growth, Processing and Properties of B-Ga2O3 Single Crystal "Chinese Doctoral Dissertation Full-text Database (Engineering Science and Technology Series I)" Jan. 15, 2019 (Jan. 15, 2019), Issue 12, pp. 1-32.

\* cited by examiner

PREPARATION METHOD OF CONDUCTIVE GALLIUM OXIDE BASED ON DEEP LEARNING AND VERTICAL BRIDGMAN GROWTH METHOD

CROSS-REFERENCE TO RELATED APPLICATIONS

This application is a national application of PCT Patent Application No. PCT/CN2021/075864, filed on Feb. 7, 2021, which claims priority to Chinese Patent Application No. 202011642153.8, filed on Dec. 31, 2020. The content of all of which is incorporate herein by reference.

FIELD

The present disclosure relates to a technical field of the preparation of gallium oxide, in particular to a preparation method of conductive gallium oxide based on deep learning and vertical Bridgman growth method.

BACKGROUND

Gallium oxide ($Ga_2O_3$) single crystal is a transparent semiconductor oxide, which belongs to a semiconductor material with wide forbidden band. Usually, $\beta$-$Ga_2O_3$ ($\beta$-Gallium oxide) is relatively stable, there are a lot of advantages of $\beta$-$Ga_2O_3$, such as large band gap, fast saturated electron drift speed, high thermal conductivity, high breakdown field strength, stable chemical properties, etc. The large band gap brings high breakdown voltage. In addition, the fast saturated electron drift speed, high thermal conductivity and stable chemical properties make $\beta$-$Ga_2O_3$ single crystal has a wide application prospect in the field of electronic devices. The vertical Bridgman growth method is one of the methods for preparing gallium oxide, while in the prior art, the conductive gallium oxide with preset carrier concentration cannot be obtained by the vertical Bridgman growth method.

Therefore, the existing technology needs to be improved.

SUMMARY

The technical problem to be solved in the present disclosure is to provide a preparation method of conductive gallium oxide based on deep learning and vertical Bridgman growth method, so as to predict and obtain a conductive gallium oxide with preset carrier concentration.

The embodiments of the present disclosure provide a prediction method of conductive gallium oxide based on deep learning and vertical Bridgman growth method, which includes steps:
obtaining a preparation data of the conductive gallium oxide single crystal, the preparation data comprises a seed crystal data, an environmental data, a control data and a raw material data, and the raw material data comprises a doping type data and a conductive doping concentration;
preprocessing the preparation data to obtain a preprocessed preparation data;
inputting the preprocessed preparation data into a trained neural network model, and obtaining a predicted property data corresponding to the conductive gallium oxide single crystal through the trained neural network model, the predicted property data comprises a predicted carrier concentration.

In the prediction method of conductive gallium oxide based on deep learning and vertical Bridgman growth method, the preprocessing the preparation data to obtain a preprocessed preparation data includes:
obtaining a preprocessed preparation data according to the seed crystal data, the environmental data, the control data and the raw material data, the preprocessed preparation data is a matrix formed by the seed data, the environmental data, the control data and the raw material data.

In the prediction method of conductive gallium oxide based on deep learning and vertical Bridgman growth method, the seed data includes: a half-height width of seed diffraction peak, a deviation value of the half-height width of seed diffraction peak and a seed diameter;
the environmental data includes: a thermal resistance value of insulating layer in high temperature area, a deviation value of the thermal resistance value of insulating layer in high temperature area, a shape factor of insulating layer in high temperature area, a thermal resistance value of insulating layer in low temperature area, a deviation value of the thermal resistance value of insulating layer in low temperature area, a shape factor of insulating layer in low temperature area and a shape factor of insulating layer in growth driving area;
the control data includes: a high temperature area input power, a high temperature area cooling power, a low temperature area input power, a low temperature area cooling power and a crucible descending speed.

In the prediction method of conductive gallium oxide based on deep learning and vertical Bridgman growth method, the obtaining a preprocessed preparation data according to the seed crystal data, the environmental data, the control data and the raw material data, includes:
determining a preparation vector according to the seed crystal data, the environmental data, the control data and the raw material data, a first element in the preparation vector is one of the half-height width of seed diffraction peak, the deviation value of the half-height width of seed diffraction peak and the seed diameter, a second element in the preparation vector is one of the thermal resistance value of insulating layer in high temperature area, the deviation value of the thermal resistance value of insulating layer in high temperature area, the shape factor of insulating layer in high temperature area, the thermal resistance value of insulating layer in low temperature area, the deviation value of the thermal resistance value of insulating layer in low temperature area, the shape factor of insulating layer in low temperature area and the shape factor of insulating layer in growth driving area, a third element in the preparation vector is one of the high temperature area input power, the high temperature area cooling power, the low temperature area input power, the low temperature area cooling power and the crucible descending speed, and a fourth element in the preparation vector is one of the doping type data and the conductive doping concentration;
determining the preprocessed preparation data according to the preparation vector.

In the prediction method of conductive gallium oxide based on deep learning and vertical Bridgman growth method, the predicted property data further includes: a predicted crack data, a predicted hybrid crystal data, a predicted half-height width of diffraction peak, a radial deviation value of the predicted half-height width of diffraction peak, a axial deviation value of the predicted half-height width of diffraction peak, a radial deviation value of the predicted carrier concentration and a axial deviation value of the predicted carrier concentration.

A preparation method of conductive gallium oxide based on deep learning and vertical Bridgman growth method which includes steps:
  obtaining a target property data of a target conductive gallium oxide single crystal, the target property data includes a target carrier concentration;
  determining a target preparation data corresponding to the target conductive gallium oxide single crystal according to the target property data and a trained neural network model, the target preparation data includes a seed crystal data, an environmental data, a control data and a raw material data, the raw material data includes a doping type data and a conductive doping concentration;
  preparing, based on the vertical Bridgman growth method, the target conductive gallium oxide single crystal according to the target preparation data.

In the preparation method of conductive gallium oxide based on deep learning and vertical Bridgman growth method, the determining a target preparation data corresponding to the target conductive gallium oxide single crystal according to the target property data and a trained neural network model includes:
  obtaining a preset preparation data, preprocessing the preset preparation data to obtain a preprocessed preset preparation data;
  inputting the preprocessed preset preparation data into the trained neural network model, and obtaining a predicted property data corresponding to the conductive gallium oxide single crystal through the trained neural network model;
  correcting the preset preparation data according to the predicted property data and the target property data to obtain the target preparation data corresponding to the target conductive gallium oxide single crystal.

In the preparation method of conductive gallium oxide based on deep learning and vertical Bridgman growth method, the trained neural network model is trained by steps:
  acquiring a training data of the conductive gallium oxide single crystal and an actual property data corresponding to the training data, the training data includes a seed crystal training data, an environmental training data, a control training data and a raw material training data, the raw material training data includes a doping type data and a conductive doping concentration;
  preprocessing the training data to obtain a preprocessed training data;
  inputting the preprocessed training data into a preset neural network model, and obtaining a predicted generated property data corresponding to the preprocessed training data through the preset neural network model, the predicted generated property data includes a predicted generated carrier concentration;
  adjusting model parameters of the preset neural network model according to the predicted generated property data and the actual property data to obtain the trained neural network model.

In the preparation method of conductive gallium oxide based on deep learning and vertical Bridgman growth method, the preset neural network model includes a feature extraction module and a fully connected module, the inputting the preprocessed training data into a preset neural network model, and obtaining a predicted generated property data corresponding to the preprocessed training data through the preset neural network model, includes:
  inputting the preprocessed training data into the feature extraction module, and obtaining a feature vector corresponding to the preprocessed training data through the feature extraction module;
  inputting the feature vector into the fully connected module, obtaining the preprocessed training data through the fully connected module, and obtaining the predicted generated property data.

A conductive gallium oxide preparation system based on deep learning and vertical Bridgman growth method which includes a memory and a processor, a computer program is stored in the memory, and the processor executes the computer program to operate the steps of the predicted method described above, or the steps of the preparation method described above.

Compared with the prior art, the embodiment of the present disclosure has the following advantages:

The preparation data is first preprocessed to obtain the preprocessed preparation data, then the preprocessed preparation data is input into the trained neural network model, and the predicted property data which corresponds to the conductive gallium oxide single crystal corresponding to the conductive gallium oxide single crystal is obtained through the trained neural network model, The trained neural network model can predict the performance of the conductive gallium oxide single crystal. Therefore, the conductive gallium oxide with preset carrier concentration can be obtained by adjusting the preparation data.

BRIEF DESCRIPTION OF THE DRAWINGS

In order to more clearly explain the embodiments of the present disclosure or the technical solutions in the prior art, the following will briefly introduce the drawings needed to be used in the embodiments of the present disclosure or the description of the prior art. It is obvious that the drawings in the following description are only some embodiments recorded in the present disclosure. For those skilled in the art, other drawings may be derived from the present drawings without paying creative labor.

DETAILED DESCRIPTION OF THE EMBODIMENTS

In order to enable those skilled in the art to better understand the scheme of the present disclosure, the technical scheme in the embodiments of the present disclosure will be clearly and completely described below in combination with the accompanying drawings in the present disclosure. Obviously, the described embodiments are only part of the embodiments of the present disclosure, not all of the embodiments of the present disclosure. Based on the embodiments of the present disclosure, all other embodiments obtained by those skilled in the art without making creative work belong to the protection scope of the present disclosure.

Figure 2:
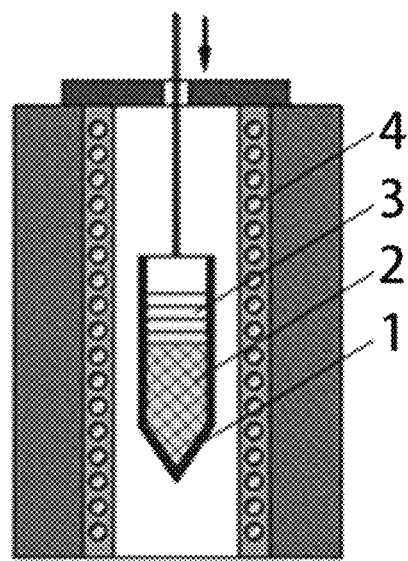
FIG. 2 is a structural diagram of a crystal growth furnace in an embodiment of the present disclosure.

Vertical Bridgman growth method, also known as Bridgeman crystal growth method, is a common crystal growth method. The material used for crystal growth is loaded in a cylindrical crucible while slowly descends and passes through a heating furnace with a certain temperature gradient, and the furnace temperature is controlled around the melting point of the material. When passing through the heating area, the material in the crucible is melted. When the crucible continues to descend, the temperature at the bottom of the crucible first drops below the melting point and the material begins to crystallize. The crystal continues to grow with the descending of the crucible, as shown in FIG. 2. It is necessary to avoid the corrosion of the crucible material while growing gallium oxide.

Various non limiting embodiments of the present disclosure will be described in detail below in combination with the drawings.

Figure 1:
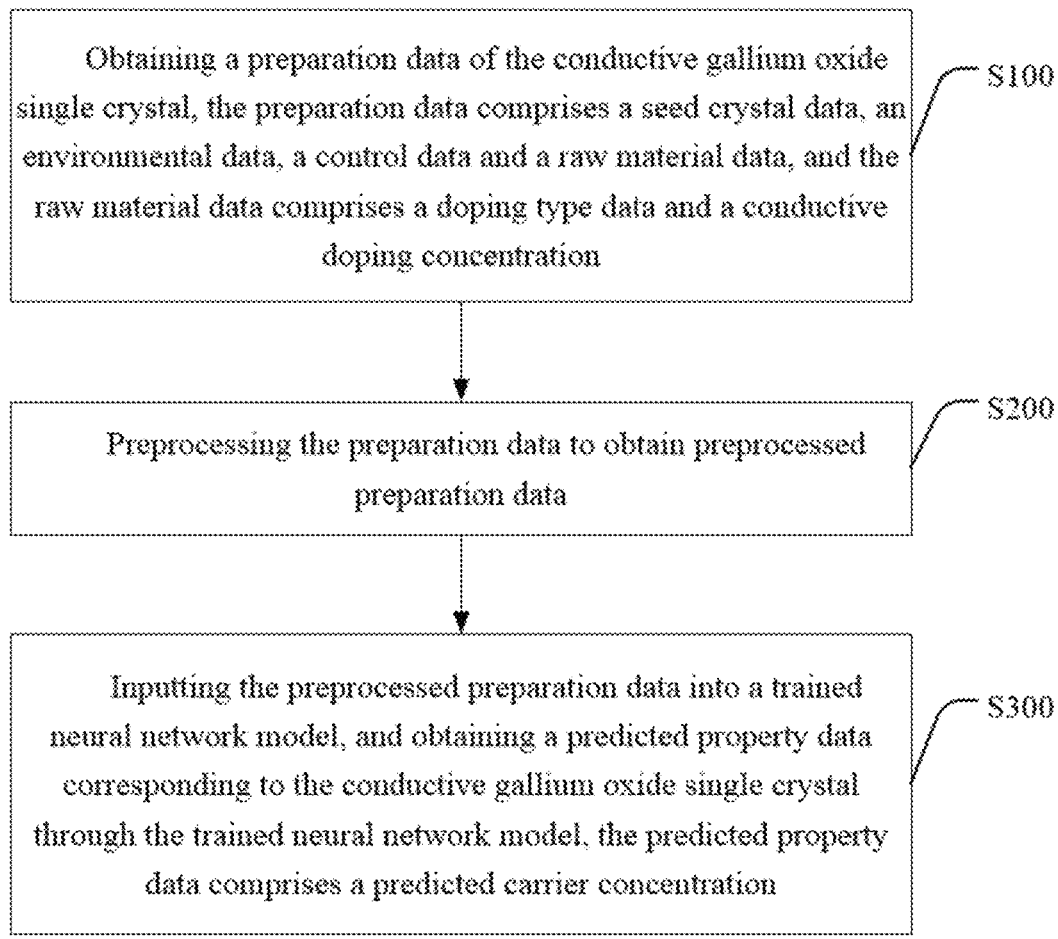
FIG. 1 is a flowchart of a prediction method of conductive gallium oxide based on deep learning and vertical Bridgman growth method in an embodiment of the present disclosure.
Figure 3:
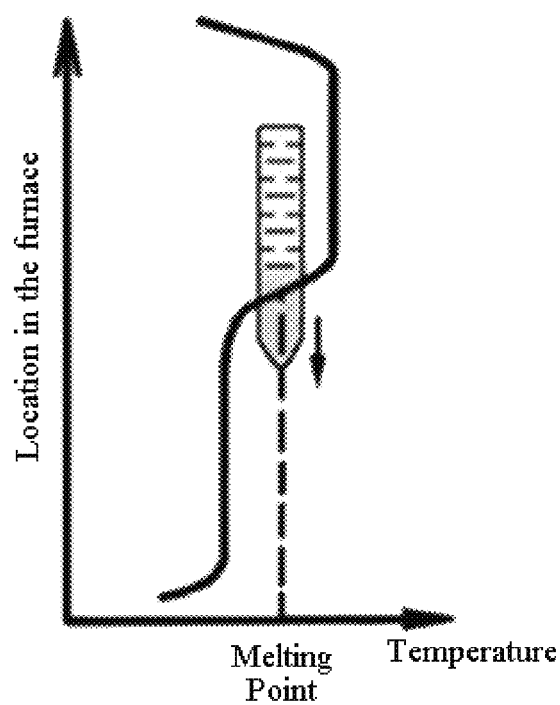
FIG. 3 is a schematic diagram of the location and temperature of the crystal in the furnace in an embodiment of the present disclosure.

Referring to FIGS. 1 to 3, a prediction method of conductive gallium oxide based on deep learning and vertical Bridgman growth method in the present disclosure is shown. In the present embodiment, the prediction method may include, for example, the following steps:

S100. Obtaining a preparation data of the conductive gallium oxide single crystal, the preparation data comprises a seed crystal data, an environmental data, a control data and a raw material data, and the raw material data comprises a doping type data and a conductive doping concentration.

The preparation data refers to a data of preparing the conductive gallium oxide single crystal, and the preparation data is the data that is configured as required, for example, when it needs to predict the performance of the conductive gallium oxide single crystal obtained under a certain preparation data, it is only necessary to determine the preparation data, and preprocess the preparation data to obtain the preprocessed preparation data, and then input the preprocessed preparation data into the trained neural network model, and obtain the preprocessed preparation data through the trained neural network model. That is, no experiment is required. After the preparation data is determined, the quality data of the conductive gallium oxide single crystal can be predicted.

In the present embodiment, the preparation data includes a seed crystal data, an environmental data, a control data and a raw material data. The seed crystal data refers to the data of the seed crystal adopted in the process of preparing the conductive gallium oxide single crystal. The environmental data refers to the data of the environment in which the crystal is placed in the process of preparing the conductive gallium oxide single crystal. The control data refers to the data of controlling crystal growth during the process of preparing the conductive gallium oxide single crystal. The raw material data refers to the data of raw material adopted in the process of preparing the conductive gallium oxide single crystal, and the concentration of the doping element is the concentration of the conductive elements doped in the gallium oxide, the doped conductive element includes Si, Ge, Sn, Zr, Hf, In, Ta, Nb, V, W, Mo, etc. The doping type data refers to the type of the doped material.

S200: Preprocessing the preparation data to obtain preprocessed preparation data.

After obtaining the preparation data, the preparation data is preprocessed to obtain the preprocessed preparation data, so that the preprocessed preparation data can be input into the trained neural network model, to process the preprocessed preparation data through the trained neural network model.

In one implementation of the embodiment, step S200 preprocessing the preparation data to obtain preprocessed preparation data includes:

S210. Obtaining a preprocessed preparation data according to the seed crystal data, the environmental data, the control data and the raw material data, the preprocessed preparation data is a matrix formed by the seed data, the environmental data, the control data and the raw material data.

After the preparation data is obtained, the preparation data is preprocessed first to obtain the preprocessed preparation data. The sub-data (such as the seed crystal data, the environmental data, the control data, and the raw material data) in the preparation data will affect each other, but it is currently not clear how much the sub-data affects each other. Therefore, it is necessary to preprocess the preparation data by rearranging and combining the sub-data in the preparation data to form the preprocessed preparation data.

In one implantation of the embodiment, the seed crystal data includes a half-height width of seed diffraction peak, a deviation value of the half-height width of seed diffraction peak and a seed diameter; the environmental data includes a thermal resistance value of insulating layer in high temperature area, a deviation value of the thermal resistance value of insulating layer in high temperature area, a shape factor of insulating layer in high temperature area, a thermal resistance value of insulating layer in low temperature area, a deviation value of the thermal resistance value of insulating layer in low temperature area, a shape factor of insulating layer in low temperature area and a shape factor of insulating layer in growth driving area; the control data includes: a high temperature area input power, a high temperature area cooling power, a low temperature area input power, a low temperature area cooling power and a crucible descending speed.

The half-height width of seed diffraction peak of the seed crystal may be tested by an X-ray diffractometer. The deviation value of the half-height width of the seed crystal diffraction peak includes a radial deviation value of the half-height width of seed crystal diffraction peak and a axial deviation value of the half-height width of seed crystal diffraction peak. The radial direction is the direction on the horizontal plane, and the axial direction is the direction perpendicular to the horizontal plane, that is, the axis in the vertical direction. The radial deviation value of the half-height width of seed crystal diffraction peak may be measured by measuring the half-height width of seed crystal diffraction peak on both sides of the radial direction of the seed crystal, to obtain the difference between the half-height widths of seed crystal diffraction peaks on both sides of the radial direction of the seed crystal, namely the radial deviation value of the half-height width of seed crystal diffraction peak. The axial deviation value of the half-height width of seed crystal diffraction peak may be measured by testing the half-height widths of seed crystal diffraction peaks on both sides of the seed crystal axis, to obtain the difference between the half-height widths of seed crystal diffraction peaks on both sides of the seed crystal axis, namely the axial deviation value of the half-height width of seed crystal diffraction peak.

When preparing conductive gallium oxide single crystal by vertical Bridgman growth method, the area where the grown crystal located is a high temperature area, the area where the melt that does not grow into crystal located is a low temperature area, the area where the melt grows into the crystal is a growth driving area, and the growth driving area is located between the high temperature area and the low temperature area. Generally, the high temperature area is located above the low temperature area. As shown in FIG. 2, when a crucible 1 is in the high temperature area, the gallium oxide in crucible 1 is a melt 3, and when the crucible 1 is in the low temperature area, the gallium oxide in the crucible 1 is a crystal 2. As shown in FIG. 2 and FIG. 3, when the crucible is in the growth driving area, the gallium oxide in the crucible grows from melt to crystal due to the decrease of temperature. When the crucible descends from high temperature area to low temperature area, the gallium oxide in the crucible gradually grows into a conductive gallium oxide single crystal. A bottom of the crucible 1 is narrowed to form a tip, and the seed crystal is located in the tip. That is, in the process of crystal growth, as the crucible descending, the crucible gradually enters the low temperature area, and the melt 3 grows from the seed crystal at the bottom of the crucible 1 into the crystal 2. Of course, the seed crystal may be placed in the tip of the crucible 1 after the gallium oxide in the crucible 1 is completely melted.

As shown in FIG. 2, an insulating layer is arranged outside an induction coil 4, which is configured to maintain the temperature. A thermal resistance value of insulating layer refers to the temperature difference between two sides of the insulating layer when a unit heat passes through the insulating layer in a unit time. The greater the thermal resistance value of the insulating layer, the stronger the ability of the insulating layer to resist heat transfer, and the better the insulation effect of the insulating layer. The thermal resistance value of insulating layer in high temperature area refers to the thermal resistance value of the insulating layer in the high temperature area, and the thermal resistance value of insulating layer in low temperature area refers to the thermal resistance value of the insulating layer in the low temperature area.

A deviation value of the thermal resistance value of insulating layer includes a radial deviation value of the thermal resistance value of insulating layer and an axial deviation value of the thermal resistance value of insulating layer. The radial deviation value of the thermal resistance value of insulating layer may be obtained by testing the thermal resistance value of the insulating layer on both sides of radial direction of the insulating layer and measuring the difference between the thermal resistance values of the insulating layers on both sides of radial direction of the insulating layer. The axial deviation value of the thermal resistance value of insulating layer may be obtained by testing the thermal resistance value of the insulating layer on both sides of axial direction of the insulating layer and measuring the difference between the thermal resistance values of the insulating layers on both sides of axial direction of the insulating layer.

Of course, a deviation value of the thermal resistance value of insulating layer in high temperature area is obtained when testing for the high temperature area, and a deviation value of the thermal resistance value of insulating layer in low temperature area can be obtained when testing for the low temperature area.

A shape factor of insulating layer refers to the value of the shape and size of the insulation area. For example, when a cylindrical insulating layer is adopted, the shape factor of insulating layer includes a diameter of the insulating layer and a height of the insulating layer. When a cubic insulating layer is adopted, the shape factor of insulating layer includes a length of insulating layer, a width of insulating layer and a height of insulating layer. Because the crystal is mainly growing in the low temperature area and growth driving area, the shape factor of insulating layer in the low temperature area and the shape factor of growth driving area may affect the growth of the crystal.

After the crucible and the crystal growth furnace are determined, the shape factor of insulating layer in the low temperature area and the shape factor of insulating layer in the growth driving area are determined. With the use of the crystal growth furnace, the thermal resistance value of insulating layer in high temperature area, the deviation value of the thermal resistance value of insulating layer in high temperature area, the shape factor of insulating layer in high temperature area, the thermal resistance value of insulating layer in low temperature area, and the deviation value of the thermal resistance value of insulating layer in low temperature area may change, but will not change in a short time. The environmental data can be retested after a certain number of crystal growth.

The high temperature area input power refers to the input power of the induction coil in the high temperature area when the crystal is growing, the low temperature area input power refers to the input power of the induction coil in the low temperature area when the crystal is growing, the high temperature area cooling power refers to the power corresponding to the cooling of the high temperature area, and the low temperature area cooling power refers to the power corresponding to the cooling of the low temperature area. Since the induction coil adopts a hollow induction coil, when cooling, a cooling medium is introduced into the induction coil to form a cooling coil, and the cooling is performed by a continuous flow of the cooling medium in the cooling coil. The cooling power of high temperature area and low temperature area may be determined according to the type of the cooling medium and the flow rate of the cooling medium. The type of cooling medium includes water, oil, and air. The flow rate of the cooling medium may be determined according to the flow velocity of the cooling medium and the diameter of the cooling coil. The crucible descending speed refers to the descending speed of crucible during crystal growth.

In one implementation of the present embodiment, the step S210 obtaining a preprocessed preparation data according to the seed crystal data, the environmental data, the control data and the raw material data includes:

S211. Determining a preparation vector according to the seed crystal data, the environmental data, the control data and the raw material data, a first element in the preparation vector is one of the half-height width of seed diffraction peak, the deviation value of the half-height width of seed diffraction peak and the seed diameter, a second element in the preparation vector is one of the thermal resistance value of insulating layer in high temperature area, the deviation value of the thermal resistance value of insulating layer in high temperature area, the shape factor of insulating layer in high temperature area, the thermal resistance value of insulating layer in low temperature area, the deviation value of the thermal resistance value of insulating layer in low temperature area, the shape factor of insulating layer in low temperature area and the shape factor of insulating layer in growth driving area, a third element in the preparation vector is one of the high temperature area input power, the high temperature area cooling power, the low temperature area input power, the low temperature area cooling power and the crucible descending speed, and a fourth element in the preparation vector is one of the doping type data and the conductive doping concentration.

S212. Determining the preprocessed preparation data according to the preparation vector.

A preparation vector (A, B, C, D) is determined according to the seed crystal data A, the environmental data B, the control data C and the raw material data D. The seed crystal data A is selected from the group consisting of: a half-height width of seed diffraction peak A1, a deviation value of the half-height width of seed diffraction peak A3 and a seed diameter A3. The environmental data B is selected from the group consisting of: a thermal resistance value of insulating layer in high temperature area B1, a deviation value of the thermal resistance value of insulating layer in high temperature area B2, a shape factor of insulating layer in high temperature area B3, a thermal resistance value of insulating layer in low temperature area B4, a deviation value of the thermal resistance value of insulating layer in low temperature area B5, a shape factor of insulating layer in low temperature area B6 and a shape factor of insulating layer in growth driving area B7. The control data C is selected from the group consisting of: a high temperature area input power C1, a high temperature area cooling power C2, a low temperature area input power C3, a low temperature area cooling power C4 and a crucible descending speed C5. The raw material data D is selected from the group consisting of: a doping type data D1 and a conductive doping concentration D2. That is, in the preparation vector (A, B, C, D), A may be one of A1, A2 and A3, B may be one of B1, B2, B3, B4, B5, B6 and B7, C may be one of C1, C2, C3, C4 and C5, and D may be one of D1 and D2. Then 210 preparation vectors can be formed.

After all preparation vectors are arranged according to the sequence numbers to form a matrix, the preprocessed preparation data is obtained.

The preprocessed preparation data are as follows:

$$\begin{bmatrix} (A1\ B1\ C1D1) & \cdots & (A1\ B7\ C1D1) & (A2\ B1\ C1D1) & \cdots & (A2\ B7\ C1D1) & (A3\ B1\ C1D1) & \cdots & (A3\ B7\ C1D1) \\ \vdots & \ddots & \vdots & \vdots & \ddots & \vdots & \vdots & \ddots & \vdots \\ (A1\ B1\ C5D1) & \cdots & (A1\ B7\ C5D1) & (A2\ B1\ C5D1) & \cdots & (A2\ B7\ C5D1) & (A3\ B1\ C5D1) & \cdots & (A3\ B7\ C5D1) \\ (A1\ B1\ C1D2) & \cdots & (A1\ B7\ C1D2) & (A2\ B1\ C1D2) & \cdots & (A2\ B7\ C1D2) & (A3\ B1\ C1D2) & \cdots & (A3\ B7\ C1D2) \\ \vdots & \ddots & \vdots & \vdots & \ddots & \vdots & \vdots & \ddots & \vdots \\ (A1\ B1\ C5D2) & \cdots & (A1\ B7\ C5D2) & (A2\ B1\ C5D2) & \cdots & (A2\ B7\ C5D2) & (A3\ B1\ C5D2) & \cdots & (A3\ B7\ C5D2) \end{bmatrix}$$

Of course, other arrangements are also adopted to obtain preprocessed preparation data.

S300. Inputting the preprocessed preparation data into a trained neural network model, and obtaining a predicted property data corresponding to the conductive gallium oxide single crystal through the trained neural network model, the predicted property data comprises a predicted carrier concentration.

The predicted property data also includes: a predicted crack data, a predicted hybrid crystal data, a predicted half-height width of diffraction peak, a radial deviation value of the predicted half-height width of diffraction peak, a axial deviation value of the predicted half-height width of diffraction peak, a radial deviation value of the predicted carrier concentration and a axial deviation value of the predicted carrier concentration.

The crack data refers to a crack level data, and a predicted crack data refers to a predicted crack level data. The cracks can be divided into multiple levels. For example, if the cracks are divided into 3 levels, the crack data are 1, 2 and 3.

A hybrid crystal data refers to a hybrid crystal level data, and a predicted hybrid crystal data refers to a predicted hybrid crystal level data. The hybrid crystal can be divided into multiple levels. For example, the hybrid crystal is divided into 3 levels, and the hybrid crystal data are 1, 2 and 3 respectively.

A predicted half-height width of diffraction peak refers to the half-height width of diffraction peak that is predicted, a radial deviation value of the half-height width of diffraction peak refers to a predicted difference between diffraction peaks on both sides of the radial direction, and a axial deviation value of the half-height width of diffraction peak refers to a predicted difference between diffraction peaks on both sides of the axial direction.

By inputting the preprocessed preparation data into a trained neural network model, the predicted property data are obtained through the neural network model. It should be noted that the predicted property data may be one or more, for example, only a predicted crack data is required.

In one implementation of the embodiments, the trained neural network model is trained by the following steps:

A100. Acquiring a training data of the conductive gallium oxide single crystal and an actual property data corresponding to the training data, the training data includes a seed crystal training data, an environmental training data, a control training data and a raw material training data, the raw material training data includes a doping type data and a conductive doping concentration.

The training data refers to the data adopted to prepare the conductive gallium oxide single crystal and be used in training, and the actual property data refers to the data of the actual properties of the prepared conductive gallium oxide single crystal. A training set is formed through the training data and the actual property data. Based on the training set, the preset neural network model is trained to obtain the trained neural network model. The seed crystal training data includes: a half-height width of seed crystal diffraction peak training data, a deviation value of the half-height width of seed crystal diffraction peak training data and a seed crystal diameter training data. The environmental training data includes: a thermal resistance value of insulating layer in high temperature area training data, a deviation value of the thermal resistance value of insulating layer in high temperature area training data, a shape factor of insulating layer in high temperature area training data, a thermal resistance value of insulating layer in low temperature area training data, a deviation value of the thermal resistance value of insulating layer in low temperature area training data, a shape factor of thermal insulating layer in low temperature area training data and a shape factor of thermal insulating layer in growth driving area training data. The raw material training data includes: a doping type training data and a conductive doping concentration training data. The control training data includes: a high temperature area input power training data, a high temperature area cooling power training data, a low temperature area input power training data, a low temperature area cooling power training data and a crucible descending speed training data. The actual property data includes: an actual carrier concentration. Of course, the actual property data may also include: an actual crack data, an actual hybrid crystal data, an actual half-height width of diffraction peak, an actual radial deviation value of the half-height width of diffraction peak, an actual axial deviation value of the half-height width of diffraction peak, an actual radial deviation value of the carrier concentration and an actual axial deviation value of the carrier concentration.

Of course, the training set may also be formed by the training data and actual property data, and the preset neural network model is trained based on the training set to obtain the trained neural network model.

When the training set is obtained by collecting the data, the conductive gallium oxide single crystal is prepared by the vertical Bridgman growth method, and the data of preparing the conductive gallium oxide single crystal is recorded as the training data. After the conductive gallium oxide single crystal is obtained, the properties of the conductive gallium oxide single crystal are analyzed to obtain the actual property data. In order to facilitate the training of neural network model, the data may be collected as much as possible to form a training set.

A200. Preprocessing the training data to obtain the preprocessed training data.

After the training data is obtained, the training data is preprocessed to obtain the preprocessed training data. The process of the preprocessing can refer to the step S200.

A300. Inputting the preprocessed training data into a preset neural network model, and obtaining a predicted generated property data corresponding to the preprocessed training data through the preset neural network model, the predicted generated property data comprises a predicted generated carrier concentration.

The preprocessed training data is input into the preset neural network model, to obtain the predicted generated property data through the preset neural network model. The predicted generated property data also includes: a predicted generated crack data, a predicted generated hybrid crystal data, a predicted generated half-height width of diffraction peak, a predicted generated radial deviation value of the half-height width of diffraction peak, a predicted generated axial deviation value of the half-height width of diffraction peak, a predicted generated radial deviation value of the carrier concentration and a predicted generated axial deviation value of the carrier concentration.

A400. Adjusting model parameters of the preset neural network model according to the predicted generated property data and the actual property data to obtain the trained neural network model.

According to the predicted generated property data and the actual property data, the model parameters of the preset neural network model is corrected, and it is continued to execute the input of the preprocessed training data into the preset neural network model, to obtain the step of predicted generated property data corresponding to the preprocessed training data through the preset neural network model (that is, step A300), until a preset training conditions are met, and the trained neural network model is obtained.

The according to the predicted generated property data and the actual property data, the model parameters of the preset neural network model is corrected, and it is continued to execute the input of the preprocessed training data into the preset neural network model, to obtain the step of predicted generated property data corresponding to the preprocessed training data through the preset neural network model, until a preset training conditions are met, and the trained neural network model is obtained, may be also described as if the preset neural network model meets the preset training conditions, the trained neural network model is obtained; and if the preset neural network model does not meet the preset training conditions, return to step A300 until the preset neural network model meets the preset training conditions, and the trained neural network model is obtained.

In an implementation of the embodiment of the present disclosure, a loss function value of the preset neural network model is determined according to the predicted generated property data and the actual property data. The model parameters of the neural network model are corrected through the loss function value. A gradient-based method is adopted to modify the parameters of the preset neural network model, and after the loss function value of the preset neural network model is determined, the gradient of the parameters of the network model, the parameters of the preset neural network model, and the preset learning rate are determined, and the modified parameters of the preset neural network model are determined.

The preset training conditions include: the loss function value meets a first preset requirement and/or the preset number of times of training of the neural network model reaches a first preset number of times.

The first preset requirement is determined according to the accuracy and efficiency of the preset neural network model, for example, the loss function value of the preset neural network model reaches a minimum value or no longer changes. The first preset number of times is the preset maximum number of training times of the neural network model, for example, 4000 times.

The loss function of the preset neural network model includes: a mean square error, a root mean square error, a mean absolute error, etc.

In an implementation of the embodiments, the preset neural network model includes: a feature extraction module and a fully connected module.

For example, the preset neural network model includes: a first convolution unit, a second convolution unit, a third convolution unit, a fourth convolution unit, and a fully connected unit. The first convolution unit includes two convolution layers and one pooling layer. The second convolution unit, the third convolution unit, and the fourth convolution unit each includes three convolution layers and one pooling layer. The fully connected unit includes three fully connected layers.

The convolutional layer and the fully connected layer are responsible for mapping and transforming an input data. This process uses parameters such as weights and biases, and requires the use of activation functions. The pooling layer is a fixed function operation. The convolutional layer plays a role in extracting features; the pooling layer performs a pooling operation on the input features to change their spatial size; and the fully connected layer connects all the data in a previous layer.

Step A300: inputting the preprocessed training data into a preset neural network model, and obtaining a predicted generated property data corresponding to the preprocessed training data through the preset neural network model includes:

A310. Inputting the preprocessed training data into the feature extraction module, and obtaining a feature vector corresponding to the preprocessed training data through the feature extraction module;

A320. Inputting the feature vector into the fully connected module, obtaining the preprocessed training data through the fully connected module, and obtaining the predicted generated property data.

The preprocessed training data is input into a preset neural network model, and the feature vector corresponding to the preprocessed training data is output through the feature extraction module in the preset neural network model, and the feature vector is input to the fully connected module, and the predicted training generated quality data corresponding to the preprocessed training data output by the fully connected module is obtained.

It can also be described as: the preprocessed training data is input into a preset neural network model, and the feature vector corresponding to the preprocessed training data is output through the feature extraction module in the preset neural network model, and the feature vector is input to the fully connected module, and the predicted training generated quality data corresponding to the preprocessed training data output by the fully connected module is obtained.

Based on the above-mentioned prediction method of conductive gallium oxide based on deep learning and vertical Bridgman growth method, the present embodiment provides a preparation method of conductive gallium oxide based on deep learning and vertical Bridgman growth method. The preparation method includes steps:

B100. Obtaining a target property data of a target conductive gallium oxide single crystal, the target property data comprises a target carrier concentration.

If the target conductive gallium oxide single crystal is to be obtained, the target property data of the target conductive gallium oxide single crystal may be determined first, that is, determining the property data of the desired conductive gallium oxide single crystal. Of course, the target property data of the target conductive gallium oxide single crystal may also be determined first, that is, determining the property data of the desired conductive gallium oxide single crystal. The target property data also includes: a target crack data, a target hybrid crystal data, a target half-height width of diffraction peak, a target radial deviation value of the half-height width of diffraction peak, a target axial deviation value of the half-height width of diffraction peak, a radial deviation value of target carrier concentration and a axial deviation value of target carrier concentration.

B200. Determining a target preparation data corresponding to the target conductive gallium oxide single crystal according to the target property data and a trained neural network model, the target preparation data comprises a seed crystal data, an environmental data, a control data and a raw material data, the raw material data comprises a doping type data and a conductive doping concentration.

The target preparation data corresponding to the target conductive gallium oxide single crystal is determined according to the target property data and the trained neural network model. Of course, target preparation data corresponding to the target conductive gallium oxide single crystal is determined according to the target property data and the trained neural network model. It should be noted that since different preparation data may obtain the same property data, the target preparation data is not unique when determining the target preparation data corresponding to the target conductive gallium oxide single crystal according to the target property data and the trained neural network model. One target preparation data is determined according to the control difficulty of each data in multiple target preparation data, so as to make the target conductive gallium oxide single crystal to be obtained more convenient.

In one implementation of the present embodiment, the B200 determining a target preparation data corresponding to the target conductive gallium oxide single crystal according to the target property data and a trained neural network model includes:

B210. Obtaining a preset preparation data, preprocessing the preset preparation data to obtain a preprocessed preset preparation data.

B220. Inputting the preprocessed preset preparation data into the trained neural network model, and obtaining a predicted property data corresponding to the conductive gallium oxide single crystal through the trained neural network model.

B230. Correcting the preset preparation data according to the predicted property data and the target property data to obtain the target preparation data corresponding to the target conductive gallium oxide single crystal.

The preset preparation data may be preset, and the preset preparation data may be preprocessed to obtain the preprocessed preset preparation data. For the preprocessing process, please refer to step S200. The preset preparation data is input into the trained neural network model to obtain the predicted property data, and then the preset preparation data is corrected according to the predicted property data and the target property data. When the difference between the predicted property data and the target property data is less than a preset threshold, the preset preparation data may be adopted as the target preparation data. When the preset preparation data is being corrected, it can be corrected automatically or manually. Of course, the loss function value can also be determined according to the predicted property data and the target property data, and then the preset preparation data can be corrected according to the loss function value. If the loss function value meets the preset correction conditions, the preset preparation data may be used as the target preparation data. The preset correction conditions include: the loss function value meets the second preset requirements and/or the correction times of the preset preparation data reach the second preset times.

It should be noted that the preset preparation data includes: a preset seed crystal data, a preset environment data a preset control data, and a preset raw material data. The preset seed crystal data includes a preset half-height width of seed diffraction peak, a preset deviation value of the half-height width of seed diffraction peak and a preset seed diameter. The preset environmental data includes a preset thermal resistance value of insulating layer in high temperature area, a preset deviation value of the thermal resistance value of insulating layer in high temperature area, a preset shape factor of insulating layer in high temperature area, a preset thermal resistance value of insulating layer in low temperature area, a preset deviation value of the thermal resistance value of insulating layer in low temperature area, a preset shape factor of insulating layer in low temperature area and a preset shape factor of insulating layer in growth driving area. The preset control data includes a preset high temperature area input power, a preset high temperature area cooling power, a preset low temperature area input power, a preset low temperature area cooling power and a preset crucible descending speed. The preset raw material data includes a preset doping type data and a preset conductive doping concentration.

B300. Preparing, based on the vertical Bridgman growth method, the target conductive gallium oxide single crystal according to the target preparation data.

After the target preparation data is obtained, the target conductive gallium oxide single crystal may be prepared according to the target preparation data based on the vertical Bridgman growth method.

Figure 4:
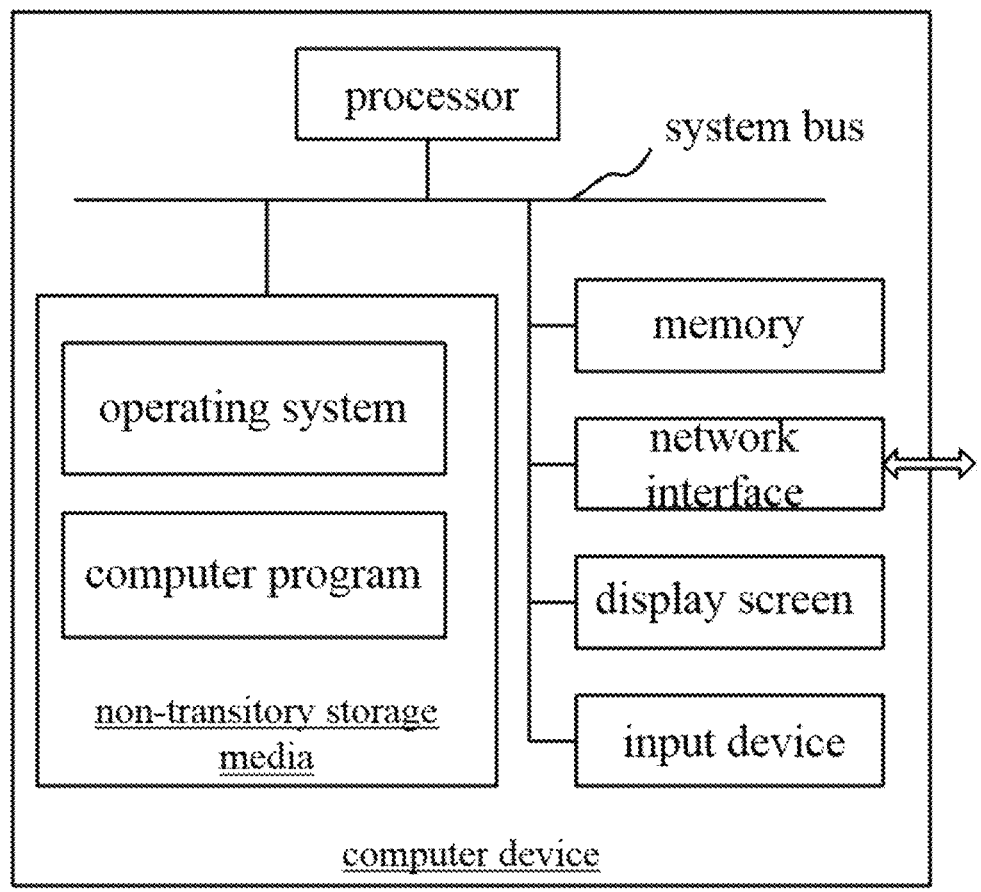
FIG. 4 is an internal structure diagram of a conductive gallium oxide preparation system based on deep learning and vertical Bridgman growth method in an embodiment of the present disclosure.

Based on the prediction method or the preparation method described above, the present disclosure provides a conductive gallium oxide preparation system based on deep learning and vertical Bridgman growth method. The system may be a computer device, and the internal structure is shown in FIG. 4. The system includes a processor, a memory, a network interface, a display screen and an input device connected via a system bus. Among them, the processor of the system is configured to provide calculation and control capabilities. The memory of the system includes a non-transitory storage media and an internal memory. The non-transitory storage media stores an operating system and a computer program. The internal memory provides an environment for the operation of the operating system and computer programs in the non-transitory storage media. The network interface of the system is used to communicate with external terminals through a network connection. The computer program is executed by the processor to realize the prediction method of conductive gallium oxide based on deep learning and vertical Bridgman growth method or the preparation method of conductive gallium oxide based on the deep learning and the vertical Bridgman growth method. The display screen of the system may be a liquid crystal display screen or an electronic ink display screen, and the input device of the system may be a touch layer covered on the display screen, or a button, a trackball or a touchpad set on the system shell, or it is an external keyboard, a touchpad, or a mouse, etc.

Those skilled in the art should understand that FIG. 4 is only a block diagram of structures related to the scheme of the present disclosure, and does not constitute a limitation on the system to which the scheme of the disclosure is applied. The specific system may include more or fewer components than those shown in the figure, or combine some components, or have different component arrangements.

In one embodiment, a conductive gallium oxide preparation system based on deep learning and vertical Bridgman growth method is provided, which includes a memory and a processor, and a computer program is stored in the memory, and the processor implements the steps of the prediction method or the preparation method when executing the computer program.

The technical features of the above embodiments may be combined in any configurations. In order to make the description concise, the possible combinations of the technical features in the above embodiments are not described in all. However, as long as there is no contradiction in the combination of these technical features, they should be considered as within the scope recorded in this description.

What is claimed is:

1. A prediction and preparation method of conductive gallium oxide based on deep learning and vertical Bridgman growth method, comprising:
  preparing a seed crystal in a crucible by the vertical Bridgman growth method, wherein the seed crystal comprises a tip portion of gallium oxide in a low temperature area of the crucible;
  determining preparation data of the conductive gallium oxide single crystal, the preparation data comprising seed crystal data measured from the seed crystal, an environmental data, a control data and a raw material data, and the raw material data comprises a doping type data and a conductive doping concentration;
  preprocessing the preparation data to obtain a preprocessed preparation data and a training set;
  training a neural network model using the training set;
  inputting the preprocessed preparation data into the trained neural network model;
  determining, by the trained neural network model, targeted quality data corresponding to the conductive gallium oxide single crystal through the trained neural network model, the targeted quality data comprising a predicted carrier concentration; and
  preparing a targeted conductive gallium oxide crystal according to the target quality data.

2. The prediction and preparation method of conductive gallium oxide based on deep learning and vertical Bridgman growth method according to claim 1, wherein preprocessing of the preparation data to obtain the preprocessed preparation data comprises:
  obtaining a preprocessed preparation data according to the seed crystal data, the environmental data, the control data and the raw material data, the preprocessed preparation data is a matrix formed by the seed data, the environmental data, the control data and the raw material data.

3. The prediction and preparation method of conductive gallium oxide based on deep learning and vertical Bridgman growth method according to claim 2, wherein the seed data comprises: a half-height width of seed diffraction peak, a deviation value of the half-height width of seed diffraction peak and a seed diameter;
  the environmental data comprises: a thermal resistance value of insulating layer in high temperature area, a deviation value of the thermal resistance value of insulating layer in high temperature area, a shape factor of insulating layer in high temperature area, a thermal resistance value of insulating layer in low temperature area, a deviation value of the thermal resistance value of insulating layer in low temperature area, a shape factor of insulating layer in low temperature area and a shape factor of insulating layer in growth driving area; and
  the control data comprises: a high temperature area input power, a high temperature area cooling power, a low temperature area input power, a low temperature area cooling power and a crucible descending speed.

4. The prediction and preparation method of conductive gallium oxide based on deep learning and vertical Bridgman growth method according to claim 3, wherein obtaining of the preprocessed preparation data according to the seed crystal data, the environmental data, the control data, and the raw material data comprises:
  determining a preparation vector according to the seed crystal data, the environmental data, the control data and the raw material data, a first element in the preparation vector is one of the half-height width of seed diffraction peak, the deviation value of the half-height width of seed diffraction peak and the seed diameter, a second element in the preparation vector is one of the thermal resistance value of insulating layer in high temperature area, the deviation value of the thermal resistance value of insulating layer in high temperature area, the shape factor of insulating layer in high temperature area, the thermal resistance value of insulating layer in low temperature area, the deviation value of the thermal resistance value of insulating layer in low temperature area, the shape factor of insulating layer in low temperature area and the shape factor of insulating layer in growth driving area, a third element in the preparation vector is one of the high temperature area input power, the high temperature area cooling power, the low temperature area input power, the low temperature area cooling power and the crucible descending speed, and a fourth element in the preparation vector is one of the doping type data and the conductive doping concentration; and determining the preprocessed preparation data according to the preparation vector.

5. The prediction and preparation method of conductive gallium oxide based on deep learning and vertical Bridgman growth method according to claim 1, wherein the predicted property data further comprises: a predicted crack data, a predicted hybrid crystal data, a predicted half-height width of diffraction peak, a radial deviation value of the predicted half-height width of diffraction peak, a axial deviation value of the predicted half-height width of diffraction peak, a radial deviation value of the predicted carrier concentration and an axial deviation value of the predicted carrier concentration.

6. A preparation method of conductive gallium oxide based on deep learning and vertical Bridgman growth method, comprising:

preparing a seed crystal in a crucible by the vertical Bridgman growth method, wherein the seed crystal comprises a tip portion of gallium oxide in a low temperature area of the crucible;

determining a target quality data of a target conductive gallium oxide single crystal, the target quality data comprising a target carrier concentration;

determining target preparation data corresponding to the target conductive gallium oxide single crystal according to the target quality data and a trained neural network model, the target preparation data comprising seed crystal data measured from the prepared seed crystal, an environmental data, a control data, and a raw material data, wherein the raw material data comprises a doping type data and a conductive doping concentration, and the trained neural network model is trained with a training set;

determining, by the trained neural network model, targeted property data corresponding to the conductive gallium oxide single crystal, the targeted quality data comprising a predicted resistivity; and preparing the target conductive gallium oxide single crystal according to the target preparation data and the target quality data.

7. The preparation method of conductive gallium oxide based on deep learning and vertical Bridgman growth method according to claim 6, wherein determining the target preparation data corresponding to the target conductive gallium oxide single crystal according to the target quality data and a trained neural network model comprises:

obtaining a preset preparation data, preprocessing the preset preparation data to obtain a preprocessed preset preparation data;

inputting the preprocessed preset preparation data into the trained neural network model, and obtaining a predicted property data corresponding to the conductive gallium oxide single crystal through the trained neural network model; and correcting the preset preparation data according to the predicted property data and the target quality data to obtain the target preparation data corresponding to the target conductive gallium oxide single crystal.

8. The preparation method of conductive gallium oxide based on deep learning and vertical Bridgman growth method according to claim 6, wherein the trained neural network model is trained by steps of:

acquiring a training data of the conductive gallium oxide single crystal and an actual property data corresponding to the training data, the training data comprises a seed crystal training data, an environmental training data, a control training data and a raw material training data, the raw material training data comprises a doping type data and a conductive doping concentration;

preprocessing the training data to obtain a preprocessed training data;

inputting the preprocessed training data into a preset neural network model, and obtaining a predicted generated property data corresponding to the preprocessed training data through the preset neural network model, the predicted generated property data comprises a predicted generated carrier concentration; and adjusting model parameters of the preset neural network model according to the predicted generated property data and the actual property data to obtain the trained neural network model.

9. The preparation method of conductive gallium oxide based on deep learning and vertical Bridgman growth method according to claim 8, wherein the preset neural network model comprises a feature extraction module and a fully connected module, and inputting the preprocessed training data into a preset neural network model, and obtaining a predicted generated property data corresponding to the preprocessed training data through the preset neural network model, comprises:

inputting the preprocessed training data into the feature extraction module, and obtaining a feature vector corresponding to the preprocessed training data through the feature extraction module; and inputting the feature vector into the fully connected module, obtaining the preprocessed training data through the fully connected module, and obtaining the predicted generated property data.

10. A conductive gallium oxide preparation system based on deep learning and vertical Bridgman growth method, comprising a non-transitory memory and a processor, a computer program is stored in the non-transitory memory, and the processor executes the computer program to operate the steps of the predicted method according to claim 1.

* * * * *